(12) United States Patent
Genin et al.

(10) Patent No.: US 6,365,612 B2
(45) Date of Patent: Apr. 2, 2002

(54) BENZOSULTAM OXAZOLIDINONE ANTIBACTERIAL AGENTS

(75) Inventors: Michael J. Genin, Paw Paw; Fred L. Ciske, Lawton, both of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/819,134

(22) Filed: Mar. 27, 2001

Related U.S. Application Data

(60) Provisional application No. 60/193,631, filed on Mar. 31, 2000.

(51) Int. Cl.[7] .................... A61K 31/428; C07D 417/04
(52) U.S. Cl. ........................................ 514/373; 548/207
(58) Field of Search ........................... 548/207; 514/373

(56) References Cited

U.S. PATENT DOCUMENTS

| | | | |
|---|---|---|---|
| 3,704,299 A | * 11/1972 | Skorez | 260/247.1 |
| 4,965,268 A | 10/1990 | Wang et al. | 514/253 |
| 5,032,605 A | 7/1991 | Wang et al. | 514/376 |
| 5,036,092 A | 7/1991 | Wang et al. | 514/376 |
| 5,036,093 A | 7/1991 | Wang et al. | 514/376 |
| 5,039,690 A | 8/1991 | Wang et al. | 514/376 |
| 5,164,510 A | 11/1992 | Brickner | 548/231 |
| 5,684,023 A | 11/1997 | Riedl et al. | 514/337 |
| 5,792,765 A | 8/1998 | Riedl et al. | 514/236.8 |

FOREIGN PATENT DOCUMENTS

| | | | |
|---|---|---|---|
| EP | 0 738 726 A1 | 10/1996 | ......... C07D/417/04 |
| WO | WO98/32438 | 7/1998 | ......... A61K/31/40 |
| WO | WO98/34929 | 8/1998 | ......... C07D/291/08 |
| WO | WO99/11264 | 3/1999 | ......... A61K/31/44 |
| WO | WO99/36069 | 7/1999 | ......... A61K/31/41 |
| WO | WO99/37641 | 7/1999 | ......... C07D/413/04 |

* cited by examiner

Primary Examiner—Laura L. Stockton
(74) Attorney, Agent, or Firm—Lucy X. Yang

(57) ABSTRACT

The present invention provides a compound of formula I

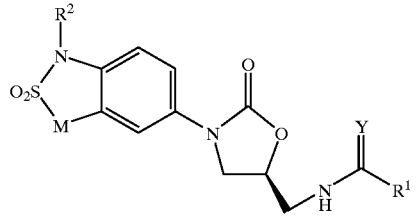

which have potent antibacterial activities.

20 Claims, No Drawings

BENZOSULTAM OXAZOLIDINONE ANTIBACTERIAL AGENTS

CROSS-REFERENCE TO RELATED APPLICATIONS

This application claims the benefit of the following provisional application: U.S. Ser. No. 60/193,631, filed Mar. 31, 2000, under 35 USC 119(e)(i).

FIELD OF THE INVENTION

The present invention relates to novel benzosultam oxazolidinones, specifically relates to N-substituted bicyclic benzosultam oxazolidinones; and their preparations. These compounds have potent antibacterial activities.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, anaerobic organisms such as bacteroides and clostridia species, and acid-fast organisms such as Mycobacterium tuberculosis and Mycobacterium avium. The benzosultam oxazolidinones of the present invention may also possess activities against gram-negative organisms such as Haemophilus influenza and Moraxella catarrhalis.

INFORMATION DISCLOSURE

U.S. Pat. No. 5,164,510 discloses 5'-indolinyloxazolidin-2-ones which are useful as antibacterial agents.

U.S. Pat. Nos. 5,036,092; 5,036,093; 5,039,690; 5,032,605 and 4,965,268 disclose aminomethyl oxazolidinyl aza cycloalkylbenzene derivatives useful as antibacterial agents.

U.S. Pat. Nos. 5,792,765 and 5,684,023 disclose substituted oxazolidinones useful as antibacterial agents.

PCT International Publications WO 98/32438, WO 98/34929, WO 99/36069, WO 9911264, discloses sultam derivatives useful in the treatment of disease states mediated by the chemokine, interleukin-8.

SUMMARY OF THE INVENTION

The present invention provides a compound of formula I

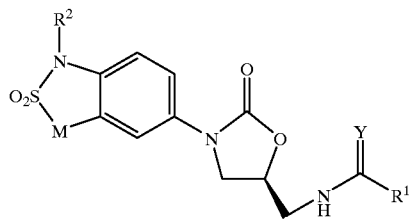

or a pharmaceutically acceptable salt thereof wherein:

$R^1$ is H, $NH_2$, $NHC_{1-4}$ alkyl, $C_{1-4}$ alkenyl, $OC_{1-4}$ alkyl, $SC_{1-4}$ alkyl, $(CH_2)_i$—$C_{3-6}$ cycloalkyl, or $C_{1-4}$ alkyl, optionally substituted with 1–3 F, 1–2 Cl or CN;

$R^2$ is H, $C_{1-12}$ alkyl optionally substituted with phenyl or CN, or $C_{2-12}$ alkyl substituted with OH, SH, $NH_2$, —$OC_{1-6}$ alkyl, —$NHC_{1-6}$ alkyl, —$NHCOC_{1-6}$ alkyl, —$NHSO_2C_{1-6}$ alkyl, —$S(O)_iC_{1-6}$ alkyl, or one to three halo;

Y is O or S;

M is —$(CH_2)_n$—, wherein n is 1 or 2 and i is 0, 1, or 2.

In another aspect, the present invention also provides:

a pharmaceutical composition comprising a compound of formula I or a pharmaceutically acceptable salt thereof, and a pharmaceutically acceptable carrier, a method for treating microbial infections in humans or other warm-blooded animals by administering to the subject in need a therapeutically effective amount of a compound of formula I or a pharmaceutically acceptable salt thereof, the use of a compound of formula I or a pharmaceutically acceptable salt thereof to prepare a medicament for treating microbial infections in humans or other warm-blooded animals, and The invention also contains novel intermediates and processes that are useful for preparing compounds of formula I.

DETAILED DESCRIPTION OF THE INVENTION

The following definitions are used, unless otherwise described.

The term alkyl, alkenyl, etc. refer to both straight and branched groups, but reference to an individual radical such as "propyl" embraces only the straight chain radical, a branched chain isomer such as "isopropyl" being specifically referred to.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

Warm-blooded animals refer to farm animal, companion animal or other type of animal.

The term "halo" refers to fluoro, chloro, bromo, or iodo

The compounds of the present invention are generally named according to the IUPAC or CAS nomenclature system.

Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

A specific value for $R^1$ is $NH_2$, —$OCH_3$, or $C_{1-4}$ alkyl.

A specific value for $R^1$ is methyl, ethyl, or isopropyl.

A specific value for $R^1$ is methyl.

A specific value for $R^1$ is ethyl.

A specific value for $R^2$ is $C_{1-6}$ alkyl.

A specific value for $R^2$ is $C_{1-6}$ alkyl substituted with CN.

A specific value for $R^2$ is benzyl.

A specific value for $R^2$ is $C_{2-6}$ alkyl substituted with OH, SH, $NH_2$, F, —$OC_{1-6}$ alkyl, —$NHC_{1-6}$ alkyl, —$NHCOC_{1-6}$ alkyl, —$NHSO_2$ $C_{1-6}$ alkyl, —$S(O)_iC_{1-6}$ alkyl, or one to three halo.

A specific value for $R^2$ is methyl or methyl substituted with CN.

A specific value for $R^2$ is ethyl substituted with fluoro or methoxy.

A specific value for $R^2$ is —$CH_2CH_2F$.

A specific value for Y is sulfur.
A specific value for Y is oxygen.
A specific value for n is 1.

These absolute configurations are called (S)-configuration according to the Cahn-Ingold-Prelog nomenclature system. It will be appreciated by those skilled in the art that compounds of the present invention may have additional chiral centers and be isolated in optically active or racemic form. It is to be understood that the present invention encompasses any racemic, optically-active, polymorphic, tautomeric, or stereoisomeric form, or mixture thereof, of a compound of the invention. It is well known in the art how to prepare the optically active forms (for example, by resolution of the racemic form by recrystallization techniques, by synthesis from optically-active starting materials, by chiral synthesis, or by chromatographic separation using a chiral stationary phase) and how to determine activity using the standard tests described herein, or using other similar tests which are well known in the art.

Examples of the present invention are:
(1) N-{[(5S)-3-(1-Methyl-2,2-dioxo-2,3-dihydro-1H-2,1-benzisothiazol-5-yl)-2-oxo-1,3-oxazolidin-5-yl]methyl}acetamide, (PNU-252307)
(2) N-({(5S)-3-[1-(2-Fluoroethyl)-2,2-dioxo-2,3-dihydro-1H-2,1-benzisothiazol-5-yl]-2-oxo-1,3-oxazolidin-5-yl}methyl)acetamide, (PNU-254380)
(3) N-({(5S)-3-[1-(2-Nitriloethyl)-2,2-dioxo-2,3-dihydro-1H-2,1-benzisothiazol-5-yl]-2-oxo-1,3-oxazolidin-5-yl}methyl)acetamide, (PNU-274919)
(4) N-({(5S)-3-[1-(2-Methoxyethyl)-2,2-dioxo-2,3-dihydro-1H-2,1-benzisothiazol-5-yl]-2-oxo-1,3-oxazolidin-5-yl}methyl)acetamide, and (PNU-276461)
(5) N-({(5S)-3-[1-(2-Fluoroethyl)-2,2-dioxo-2,3-dihydro-1H-2,1-benzisothiazol-5-yl]-2-oxo-1,3-oxazolidin-5-yl}methyl)ethanethiomide. (PNU-254646)

The following describes the preparation of compounds of the present invention. All of the starting materials are prepared by procedures described herein or by procedures that would be well known to one of ordinary skill in organic chemistry.

As shown in CHART I, nitrobenzosultam 1, (can be obtained according to the methods described in J. Het. Chem. 1986, 23, 1645), is first converted to a sodium salt by treatment with a suitable base such as sodium bicarbonate. The nitrogen at the 1-position can then be alkylated by treatment with a variety of alkylating agents including alkyl halides and heating in a suitable solvent such as DMF. These compounds of general structure 2 can be reduced by catalytic hydrogenation in the presence of a suitable catalyst such as palladium on carbon in a suitable solvent such as ethyl acetate, THF, methanol or combinations thereof to afford 5-aminobenzosultams 3. When 3 are treated with magnesium triflate and N-[(2S)oxiranylmethyl] acetamide, prepared by the method of Schaus and Jacobsen (Tetrahedron Lett. 1996, 37, 7937), in a suitable solvent, preferably acetonitrile, the chiral alcohols 4 can be obtained. These compounds can be cyclized to the desired oxazolidinones 5 by reaction with a carbonyl equivalent such as carbonyl diimidazole or preferably N,N'-disuccinimidyl carbonate with an appropriate base such as triethylamine in a mixed solvent system such as acetonitrile/DMF. Additionally, these oxazolidinone amides can be reacted with a sulfurating agent such as Lawesson's Reagent in an appropriate solvent such as THF to obtain the corresponding thioamides 6.

CHART I

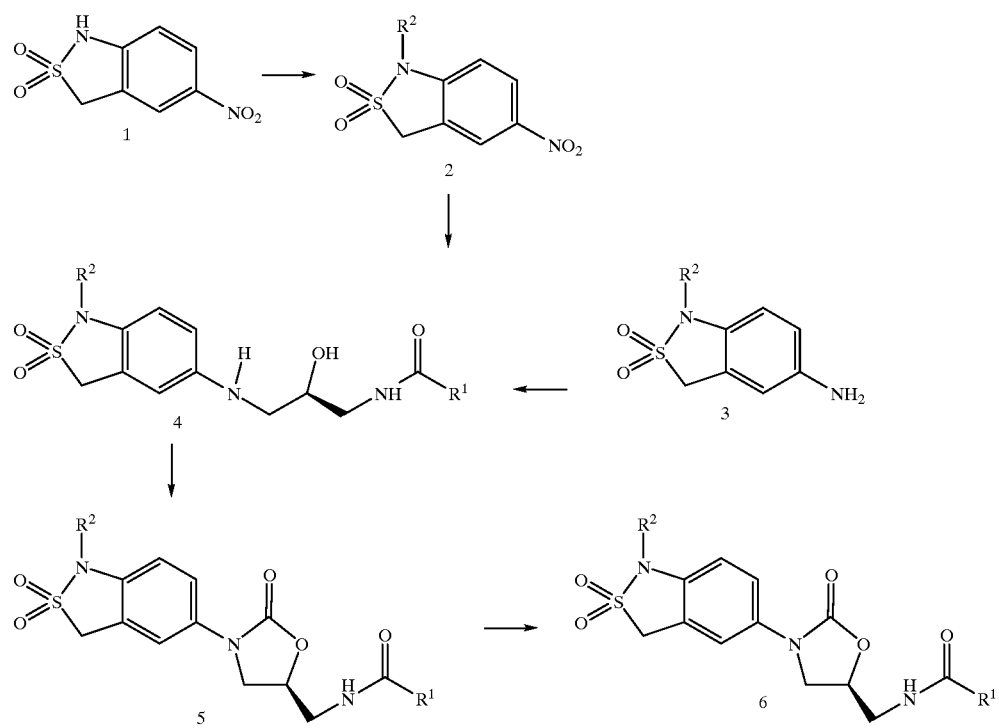

In CHART II, the compounds wherein n=2 can be prepared from the known intermediate 7 (Sianesi, E. et al. *Chem. Ber.* 1971, 104, 1880). Nitration of structure 7 provides structure 8. The remaining synthetic steps which lead to structure 9 are similar to the procedures outlined in CHART I.

CHART II

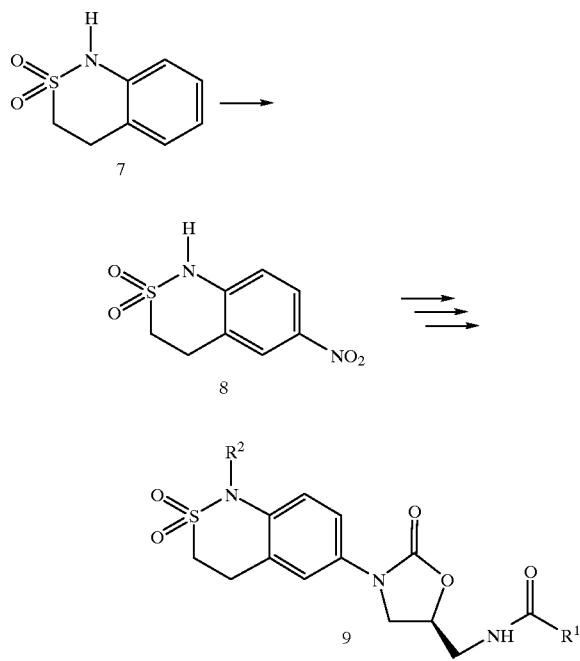

It will be apparent to those skilled in the art that the described synthetic procedures are merely representative in nature and that alternative synthetic processes are known to one of ordinary skill in organic chemistry.

The pharmaceutical compositions of this invention may be prepared by combining acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compounds of formula I according to this invention.

The quantity of active component, that is the compound of formula I according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 500, preferably about 1.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds according to formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the abovementioned antibacterially effective amount of dosage. The compounds of formula I according to this invention are advantageously administered orally in solid and liquid dosage forms.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, (x-ketoglutarate, maleate, fumarate, benzenesulfonate and a-glycerophosphate. Suitable inorganic salts may also be formed, including hydrobromide, hydrochloride, sulfate, nitrate, bicarbonate, and carbonate salts.

EXAMPLES

Example 1

Preparation of N-{[(5S)-3-(1-methyl-2,2-dioxo-2,3-dihydro-1H-2,1-benzisothiazol-5-yl)-2-oxo-1,3-oxazolidin-5-yl]methyl}acetamide (PNU-252307)

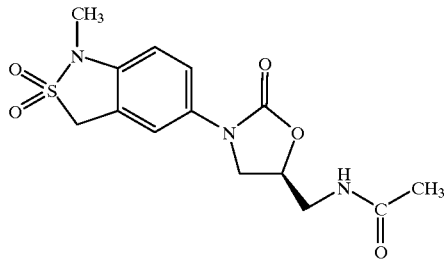

Step 1: Preparation of 1-methyl-5-nitro-1,3-dihydro-2H-2,1-benzisothiazole-2,2-dione:

$NaHCO_3$ (0.2 g, 2.4 mmol) is dissolved in $H_2O$ (3 mL) and 5-Nitro-1,3-dihydro-2H-2,1-benzisothiazole-2,2-dione (1) (0.41 g, 1.9 mmol) is added with stirring. The mixture is heated to 80° C. for 0.5 hrs and a yellow solid formed. The mixture is cooled to 0° C. and filtered. The solid is washed with cold $H_2O$ (5 mL) then with cold EtOH (15 mL). The yellow solid thus obtained is dried under high vacuum then dissolved in dry DMF (3.5 mL). Iodomethane (0.15 mL, 2.1 mmol) is added and the solution heated to 100° C. for 2 hrs. The solution is cooled to room temperature then poured into ice water (50 mL). The solid is collected by filtration and gave crystals (0.27 g, 62%) after recrystallization from EtOH. Mp 214–6° C. HRMS (FAB) calcd for $C_8H_8N_2O_4S$ $+H_1$ 229.0283, found 229.0280.

Step 2: Preparation of N-{(2R)-2-hydroxy-3-[(1-methyl-2,2-dioxo-2,3-dihydro-1H-2,1-benzisothiazol-5-yl)amino]propyl}acetamide:

The product of Step 1 (0.20 g, 0.88 mmol) is dissolved into EtOAc (30 mL) in a Parr bottle and 10% Pd/C (100 mg) added under nitrogen. The mixture is hydrogenated on a Parr apparatus for 2 hrs at 30 psi. Filtration and evaporation of solvent gave a white solid. This material is added to a mixture of N-[(2S)oxiranylmethyl] acetamide (0.81 g, 7.0 mmol) and magnesium trifluoromethanesulfonate (0.42 g, 1.3 mmol) in dry $CH_3CN$ (10 mL) at room temperature. After 20 hrs solvent is evaporated and the residue purified by chromatography (4%MeOH/$CH_2Cl_2$) to give a foamy solid (0.23 g, 79%). HRMS (FAB) calcd for $C_{13}H_{19}N_3O_4S$ $+H_1$ 314.1174, found 314.1174.

Step: 3 Preparation of N-{[(5S)-3-(1-methyl-2,2-dioxo-2,3-dihydro-1H-2,1-benzisothiazol-5-yl)-2-oxo-1,3-oxazolidin-5-yl]methyl}acetamide PNU-252307

The previous product (0.20 g, 0.63 mmol) is dissolved in $CH_3CN$ (5 mL) and DMF (2.5 mL). N,N'-Disuccinimidyl carbonate (0.23 g, 0.90 mmol) is added followed by triethylamine (0.26 mL, 1.9 mmol) and the mixture stirred at room temperature for 20 hrs. The mixture is poured into $CH_2Cl_2$ (30 mL) and washed with $H_2O$ (3×20 mL). The organics are dried ($Na_2SO_4$), filtered and solvent evaporated. The residue is chromatographed (3%MeOH/$CH_2Cl_2$) to obtain a white solid (0.142 g, 66%). Mp 84–6° C. HRMS (FAB) calcd for $C_{14}H_{17}N_3O_5S$ $+H_1$ 340.0967, found 340.0965.

Example 2

Preparation of N-({(5S)-3-[1-(2-fluoroethyl)-2,2-dioxo-2,3-dihydro-1H-2,1-benzisothiazol-5-yl]-2-oxo-1,3-oxazolidin-5-yl}methyl)acetamide PNU-254380

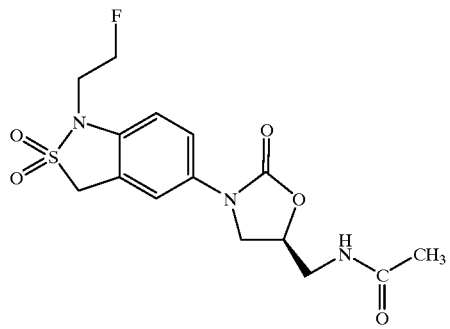

Step 1: Preparation of 1-(2-fluoroethyl)-5-nitro-1,3-dihydro-2H-2,1-benzisothiazole-2,2-dione $NaHCO_3$ (0.93 g, 11.0 mmol) is dissolved in $H_2O$ (15 mL) and 5-Nitro-1,3-dihydro-2H-2,1-benzisothiazole-2,2-dione (1) (1.90 g, 8.9 mmol) is added with stirring. The mixture is heated to 80° C. for 0.5 hrs and a yellow solid formed. The mixture is cooled to 0° C. and filtered. The solid is washed with cold $H_2O$ (15 mL) then with cold EtOH (25 mL). The yellow solid thus obtained is dried under high vacuum then dissolved in dry DMF (15 mL). 1-Bromo-2-fluoroethane (1.52 mL, 20.0 mmol) is added and the solution heated to 100° C. for 4 hrs. The solution is cooled to room temperature then poured into ice water (50 mL). The solid is collected by filtration and gave crystals (1.55 g, 67%) after recrystallization from EtOH. Mp 142–4° C. HRMS (FAB) calcd for $C_9H_9FN_2O_4S$ $+NA_1$ 283.0165, found 283.0166.

Step 2: Preparation of 5-amino-1-(2-fluoroethyl)-1,3-dihydro-2H-2,1-benzisothiazole-2,2-dione The product of Step 1 (1.25 g, 4.8 mmol) is dissolved into EtOAc (30 mL) in a Parr bottle and 10% Pd/C (100 mg) added under nitrogen. The mixture is hydrogenated on a Parr apparatus for 4 hrs at 40 psi. Filtration and evaporation of solvent gave a solid (1.1 g, 99%). Mp 119–21° C. HRMS (FAB) calcd for $C_9H_{11}FN_2O_2S$ $+H_1$ 231.0603, found 231.0610.

Step 3: N-({(5S)-3-[1-(2-fluoroethyl)-2,2-dioxo-2,3-dihydro-1H-2,1-benzisothiazol-5-yl}-2-oxo-1,3-oxazolidin-5-yl]methyl)acetamide PNU-254380

The previous 5-amino product (0.95 g, 4.1 mmol) is added to a mixture of N-[(2S)oxiranylmethyl] acetamide (0.81 g, 7.0 mmol) and magnesium trifluoromethanesulfonate (2.0 g, 6.2 mmol) in dry $CH_3CN$ (45 mL) at room temperature. After 20 hrs solvent is evaporated and the residue chromatographed (4% MeOH/$CH_2Cl_2$). The intermediate product is dissolved in $CH_3CN$ (25 mL) and DMF (12 mL). N,N'-Disuccinimidyl carbonate (2.25 g, 9.0 mmol) is added followed by triethylamine (2.6 mL, 18.8 mmol) and the mixture stirred at room temperature for 20 hrs. The mixture is poured into $CH_2Cl_2$ (30 mL) and washed with $H_2O$ (3×20 mL). The organics are dried ($Na_2SO_4$), filtered and solvent evaporated. The residue is chromatographed (3%MeOH/$CH_2Cl_2$) to obtain a white solid (0.58 g, 38%). Mp 84–7° C. (dec). HRMS (FAB) calcd for $C_{15}H_{18}FN_3O_5S$ $+H_1$ 372.1029, found 372.1021.

Example 3

Preparation of N-({(5S)-3-[1-(2-nitriloethyl)-2,2-dioxo-2,3-dihydro-1H-2,1-benzisothiazol-5-yl]-2-oxo-1,3-oxazolidin-5-yl}methyl)acetamide PNU-274919

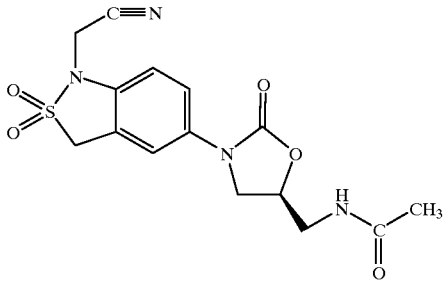

Step 1: Preparation of 2-(5-nitro-2,2-dioxo-2,3-dihydro-1H-2,1-benzisothiazol-1-yl)acetonitrile NaHCO$_3$ (1.48 g, 17.6 mmol) is dissolved in H$_2$O (20 mL) and 5-Nitro-1,3-dihydro-2H-2,1-benzisothiazole-2,2-dione (1) (3.17 g, 14.8 mmol) is added with stirring. The mixture is heated to 80° C. for 0.5 hrs and a yellow solid formed. The mixture is cooled to 0° C. and filtered. The solid is washed with cold H$_2$O (25 mL) then with cold EtOH (45 mL). The yellow solid thus obtained (intermediate sodium salt) is dried under high vacuum. A portion of this material (1.0 g, 4.2 mmol) is dissolved in dry DMF (7.0 mL). Bromoacetonitrile (0.34 mL, 5.0 mmol) is added and the solution heated to 100° C. for 2 hrs. The solution is cooled to room temperature then poured into ice water (50 mL). The solid is collected by filtration and gave an off-white solid (0.73 g, 69%) after recrystallization from EtOH. Mp 200–2° C. HRMS (FAB) calcd for C$_9$H$_7$N$_3$O$_4$S +H$_1$ 254.0235, found 254.0235.

Step 2: N-({(5S)-3-[1-(2-nitriloethyl)-2,2-dioxo-2,3-dihydro-1H-2,1-benzisothiazol-5-]-2-oxo-1,3-oxazolidin-5-yl}methyl)acetamide PNU-274919

The product of Step 1 (0.73 g, 2.9 mmol) is dissolved into EtOAc (30 mL) in a Parr bottle and 10% Pd/C (100 mg) added under nitrogen. The mixture is hydrogenated on a Parr apparatus for 2 hrs at 40 psi. Filtration and evaporation of solvent gave a yellow solid which is added to a mixture of N-[(2S)oxiranylmethyl]acetamide (0.97 g, 8.0 mmol) and magnesium trifluoromethanesulfonate (1.3 g, 4.0 mmol) in dry CH$_3$CN (30 mL) at room temperature. After 20 hrs solvent is evaporated and the residue chromatographed (4% MeOH/CH$_2$Cl$_2$). The intermediate product is dissolved in CH$_3$CN (20 mL) and DMF (10 mL). N,N'-Disuccinimidyl carbonate (1.0 g, 4.1 mmol) is added followed by triethylamine (1.2 mL, 8.7 mmol) and the mixture stirred at room temperature for 20 hrs. The mixture is poured into CH$_2$Cl$_2$ (30 mL) and washed with H$_2$O (3×20 mL). The organics are dried (Na$_2$SO$_4$), filtered and solvent evaporated. The residue is chromatographed (3%MeOH/CH$_2$Cl$_2$) to obtain a pale yellow solid (0.12 g, 11%). Mp 124–6° C. (dec). HRMS (FAB) calcd for C$_{15}$H$_{16}$N$_4$O$_5$S +H$_1$ 365.0919, found 365.0915.

Example 4

Preparation of N-({(5S)-3-[1-(2-methoxyethyl)-2,2-dioxo-2,3-dihydro-1H2,1-benzisothiazol-5-yl]-2-oxo-1,3-oxazolidin-5-yl}methyl)acetamide PNU-276461

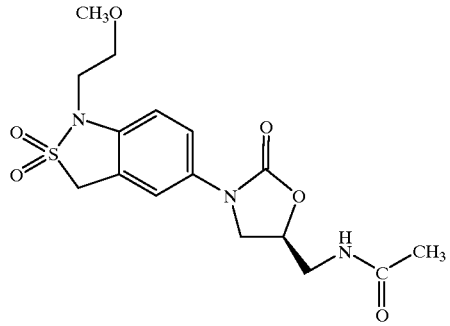

Step 1-(2-methoxyethyl)-5-nitro-1,3-dihydro-2H-2,1-benzisothiazole-2,2-dione

NaHCO$_3$ (1.48 g, 17.6 mmol) is dissolved in H$_2$O (20 mL) and 5-Nitro-1,3-dihydro-2H-2,1-benzisothiazole-2,2-dione (1) (3.17 g, 14.8 mmol) is added with stirring. The mixture is heated to 80° C. for 0.5 hrs and a yellow solid formed. The mixture is cooled to 0° C. and filtered. The solid is washed with cold H$_2$O (25 mL) then with cold EtOH (45 mL). The yellow solid thus obtained (intermediate sodium salt) is dried under high vacuum. A portion of this material (1.0 g, 4.2 mmol) is dissolved in dry DMF (7.0 mL). 2-Bromoethyl methyl ether (1.41 mL, 15.0 mmol) and potassium iodide (10 mg) are added and the solution heated to 130° C. for 5 days. The solution is cooled to room temperature then poured into ice water (50 mL). The solid is collected by filtration and gave a solid (0.77 g, 67%) after chromatography (50% EtOAc/Heptane). Mp 130–2° C. HRMS (FAB) calcd for C$_{10}$H$_{12}$N$_2$O$_5$S +H$_1$ 273.0545, found 273.0548.

Step 2: N-({(5S)-3-[1-(2-methoxyethyl)-2,2-dioxo-2,3-dihydro-1H-2,1-benzisothiazol-5-yl]-2-oxo-1,3-oxazolidin-5-yl}methyl)acetamide PNU-276461

The product of Step 1 (0.70 g, 2.6 mmol) is dissolved into EtOAc (30 mL) in a Parr bottle and 10% Pd/C (100 mg) added under nitrogen. The mixture is hydrogenated on a Parr apparatus for 2 hrs at 40 psi. Filtration and evaporation of solvent gave a residue which is added to a mixture of N-[(2S)oxiranylmethyl]acetamide (0.115 g, 1.0 mmol) and magnesium trifluoromethanesulfonate (0.32 g, 1.0 mmol) in dry CH$_3$CN (10 mL) at room temperature. After 20 hrs solvent is evaporated and the residue is dissolved in CH$_3$CN (10 mL) and DMF (5 mL). N,N'-Disuccinimidyl carbonate (0.30 g, 1.2 mmol) is added followed by triethylamine (0.34 mL, 2.4 mmol) and the mixture stirred at room temperature for 20 hrs. The mixture is poured into CH$_2$Cl$_2$ (30 mL) and washed with H$_2$O (3×20 mL). The organics are dried (Na$_2$SO$_4$), filtered and solvent evaporated. The residue is chromatographed (3%MeOH/CH$_2$Cl$_2$) to obtain a pale yellow foamy solid (0.114 g, 38%). HRMS (EI) calcd for C$_{16}$H$_{21}$N$_3$O$_6$S 383.1151, found 383.1149.

Example 5
Preparation of N-({(5S)-3-[1-(2-fluoroethyl)-2,2-dioxo-2,3-dihydro-1H-2,1-benzisothiazol-5-yl]-2-oxo-1,3-oxazolidin-5-yl}methyl)ethanethioamide PNU-254646

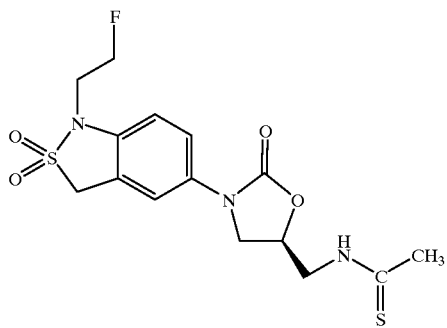

The product from example 2 (0.195 g, 0.52 mmol) and Lawesson's Reagent (0.21 g, 0.52 mmol) are stirred in dry THF (20 mL) and heated to reflux for 20 hrs. The mixture is cooled to room temperature and solvent evaporated. The residue is chromatographed (4%MeOH/CH$_2$Cl$_2$) to give a solid (0.178 g, 88%). Mp 90–3° C. (dec). HRMS (FAB) calcd for C$_{15}$H$_{18}$FN$_3$O$_4$S$_2$ +H$_1$ 388.0801, found 388.0805.

What is claimed is:
1. A compound of formula I

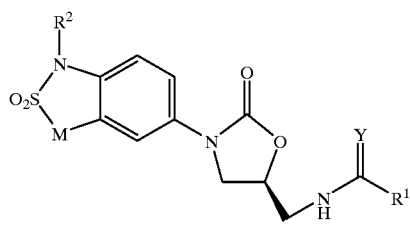

or a pharmaceutically acceptable salt thereof wherein:
R$^1$ is
  a) H,
  b) NH$_2$,
  c) NHC$_{1-6}$ alkyl,
  d) C$_{1-6}$ alkenyl,
  e) OC$_{1-6}$ alkyl, SC$_{1-6}$ alkyl,
  f) (CH$_2$)$_i$—C$_{3-6}$ cycloalkyl, or
  g) C$_{1-6}$ alkyl, optionally substituted with one to three halo;
R$^2$ is
  a) H,
  b) C$_{1-12}$ alkyl, optionally substituted with phenyl or CN, or
  c) C$_{2-12}$ alkyl substituted with OH, SH, NH$_2$, —OC$_{1-6}$ alkyl, —NHC$_{1-6}$ alkyl, —NHCOC$_{1-6}$ alkyl, —NHSO$_2$C$_{1-6}$ alkyl, —S(O)$_i$C$_{1-6}$ alkyl, or one to three halo;
Y is O or S;
M is —(CH$_2$)$_n$—, wherein n is 1 or 2; and
i is 0, 1, or 2.
2. A compound of claim 1 wherein R$^1$ is NH$_2$, —OCH$_3$, or C$_{1-4}$ alkyl.
3. A compound of claim 1 wherein R$^1$ is methyl.
4. A compound of claim 1 wherein R$^1$ is ethyl.
5. A compound of claim 1 wherein R$^2$ is C$_{1-6}$ alkyl, optionally substituted with phenyl or CN.
6. A compound of claim 1 wherein R$^2$ is C$_{2-6}$ alkyl substituted with OH, SH, NH$_2$, F, —OC$_{1-6}$ alkyl, —NHC$_{1-6}$ alkyl, —NHCOC$_{1-6}$ alkyl, —NHSO$_2$ C$_{1-6}$ alkyl, or —S(O)$_i$ C$_{1-6}$ alkyl.
7. A compound of claim 1 wherein R$^2$ is C$_{1-4}$ alkyl optionally substituted with CN, or C$_{2-4}$ alkyl substituted with fluoro or OC$_{1-4}$ alkyl.
8. A compound of claim 1 wherein R$^1$ is C$_{1-4}$ alkyl; R$^2$ is C$_{1-4}$ alkyl optionally substituted with CN, or C$_{2-4}$ alkyl substituted with fluoro or OC$_{1-4}$ alkyl; Y is sulfur or oxygen; and n is 1.
9. A compound of claim 8 wherein Y is sulfur.
10. A compound of claim 8 wherein R$^1$ is CH$_3$ or CH$_2$CN; R$^2$ is CH$_2$CH$_2$F or CH$_2$CH$_2$OCH$_3$; Y is sulfur or oxygen, n is 1.
11. A compound of claim 10 wherein Y is sulfur.
12. A compound of claim 1 which is
  (a) N-{[(5S)-3-(1-Methyl-2,2-dioxo-2,3-dihydro-1H-2,1-benzisothiazol-5-yl)-2-oxo1,3-oxazolidin-5-yl]methyl}acetamide,
  (b) N-({(5S)-3-[1-(2-Fluoroethyl)-2,2-dioxo-2,3-dihydro-1H-2,1-benzisothiazol-5-yl]-2-oxo-1,3-oxazolidin-5-yl}methyl)acetamide,
  (c) N-({(5S)-3-[1-(2-Nitriloethyl)-2,2-dioxo-2,3-dihydro-1H-2,1-benzisothiazol-5-yl]-2-oxo-1,3-oxazolidin-5-yl}methyl)acetamide,
  (d) N-({(5S)-3-[1-(2-Methoxyethyl)-2,2-dioxo-2,3-dihydro-1H-2,1-benzisothiazol-5-yl]-2-oxo-1,3-oxazolidin-5-yl}methyl)acetamide, or
  (e) N-({(5S)-3-[1-(2-Fluoroethyl)-2,2-dioxo-2,3-dihydro-1H-2,1-benzisothiazol-5-yl]-2-oxo-1,3-oxazolidin-5-yl}methyl)ethanethioamide.
13. A compound of claim 1 which is N-({(5S)-3-[1-(2-Fluoroethyl)-2,2-dioxo-2,3-dihydro-1H-2,1-benzisothiazol-5-yl]-2-oxo-1,3-oxazolidin-5-yl}methyl)ethanethioamide.
14. A method for treating microbial infections in mammals comprising: administering an effective amount of a compound of formula I as shown in claim 1, to said mammal.
15. The method of claim 14 wherein said compound of formula I is administered orally, parenterally, transdermally, or topically in a pharmaceutical composition.
16. The method of claim 14 wherein said compound is administered in an amount of from about 0.1 to about 500 mg/kg of body weight/day.
17. The method of claim 14 wherein said compound is administered in an amount of from about 1 to about 50 mg/kg of body weight/day.
18. A method for treating microbial infections of claim 14 wherein the infection is skin infection.
19. A method for treating microbial infections of claim 14 wherein the infection is eye infection.
20. A pharmaceutical composition comprising a compound of claim 1 and a pharmaceutically acceptable carrier.

* * * * *